United States Patent [19]
Perdrizet

[11] Patent Number: 5,955,111
[45] Date of Patent: Sep. 21, 1999

[54] METHODS AND COMPOSITIONS FOR INDUCING PRODUCTION OF STRESS PROTEINS

[75] Inventor: George A. Perdrizet, South Glastonbury, Conn.

[73] Assignee: Hartford Hospital, Hartford, Conn.

[21] Appl. No.: 08/727,114

[22] Filed: Oct. 8, 1996

[51] Int. Cl.⁶ .......................... A01N 59/16; A01N 55/04; A01N 55/02
[52] U.S. Cl. .......................... 424/643; 424/641; 424/650; 514/493; 514/494
[58] Field of Search .................................. 424/617, 641, 424/643, 650; 514/492, 493, 494, 836

[56] References Cited

U.S. PATENT DOCUMENTS

| | | | |
|---|---|---|---|
| 5,389,383 | 2/1995 | Huth | 424/650 |
| 5,614,553 | 3/1997 | Ashmead et al. | 514/505 |
| 5,618,838 | 4/1997 | Chevion et al. | 514/492 |

FOREIGN PATENT DOCUMENTS

| | | |
|---|---|---|
| 0 245 669 A2 | 11/1987 | European Pat. Off. |
| 372 676 | 6/1990 | European Pat. Off. |
| 521 787 | 1/1993 | European Pat. Off. |
| 91/16909 | 11/1991 | WIPO |
| 93/10777 | 6/1993 | WIPO |
| 95/00140 | 1/1995 | WIPO |
| 95/00176 | 1/1995 | WIPO |
| 95/35305 | 12/1995 | WIPO |
| 97/18088 | 2/1998 | WIPO |

OTHER PUBLICATIONS

C.G. Taylor et al., "Comparison of Zn and Vitamin E for Protection Against Hyperoxia–Induced Lung Damage," *Free Radical Biology & Medicine*, 22(3):543–550 (1997).

D. Willis et al., "Heme Oxygenase: A Novel Target for the Modulation of the Inflammatory Response," *Nature Medicine*, 2(1):87–90 (Jan. 1996).

Michal Laniado–Schwartzman et al., "Heme Oxygenase Induction with Attenuation of Experimentally Induced Corneal Inflammation," *Biochemical Pharmacology*, 53:1069–1075 (1997).

G. Russotti et al., "Induction of Tolerance to Hypothermia by Previous Heat Shock Using Human Fibroblasts in Culture," *Cryobiology*, 33:567–580 (1996).

Kadoya, Chitoshi et al., "Preischemic But Not Postischemic Zinc Protoporphyrin Treatment Reduces Infarct Size and Edema Accumulation After Temporary Focal Cerebral Ischemia in Rats," *Stroke*, vol. 26, No. 6:1035–1038 (1995).

Cornwall, Mark W., "Zinc Iontophoresis to Treat Ischemic Skin Ulcers," *Physical Therapy*, vol. 61, No. 3:359–360 (1981).

Bianco, Jesus A., et al., "Technetium–99m($Sn^{2+}$) Pyrophosphate in Ischemic and Infarcted Dog Myocardium in Early Stages of Acute Coronary Occlusion: Histochemical and Tissue–Counting Comparisons," *J. Nucl. Med.*, vol. 24, No. 6:485–491 (1983).

Babenko, G.A. et al., "Use of Zinc Valerate in the Complex Treatment of Ischemic Disease," *Vracebnoe Delo* vol. 8, pp:21–23 (1971).

Duquesnoy, Rene J., "Stress Protein Research in Transplantation," *Cell Stress & Chaperones*, vol. 1, No. 1:2–4 (1996).

Perdrizet, George A., "Heat Shock and Tissue Protection," *New Horizons*, vol. 3, No. 2:312–320 (1995).

Perdrizet, George A., "The Heat Shock Response and Organ Transplantation," *Transplantation Reviews*, vol. 10, No. 2:78–98 (1996).

Perdrizet, George A. et al., "Heat Shock Protects Pig Kidneys Against Warm Ischemic Injury," *Transplantation Proceedings*, vol. 22, No. 2:460–461 (1990).

Perdrizet, George A. et al., "Heat Shock and Recovery Protects Renal Allografts From Warm Ischemic Injury and Enhances HSP72 Production," *Transplantation Proceedings*, vol. 25, No. 1:1670–1673 (1993).

Perdrizet, George A. et al., "Heat Shock and Recovery Protects Pancreatic Islets From Warm Ischemic Injury," *Transplantation Proceedings*, vol. 26, No. 6:3477–3478 (1994).

Chatson, George et al., "Heat Shock Protects Kidneys Against Warm Ischemic Injury," *Current Surgery*, vol. 47, No. 6:420–423 (1990).

Wang, Bernadette, H. and Udelsman, Robert, "Improved Musculocutaneous Flap Survival with Induction of Heat Shock Protein," *Abstract, Cold Spring Harbor Laboratory Symposium on Molecular Chaperones and the Heat Shock Response*, Cold Spring Harbor, New York, May 1–5, 1996, p.343.

Hilden, Shirley, "Stress Proteins in Renal Ischemia," eds. John J. Lemasters, Constance Oliver, *Cell Biology of Trauma* Chapter 15, 227–250 (1995).

Perdrizet, George A. et al., "Stress Conditioning: A Novel Approach to Organ Preservation," *Current Surgery*, vol. 46, No. 1:23–26 (1989).

(List continued on next page.)

*Primary Examiner*—Jon P. Weber
*Assistant Examiner*—Susan Hanley
*Attorney, Agent, or Firm*—Hamilton, Brook, Smith & Reynolds, P.C.

[57] ABSTRACT

The present invention relates to compositions and methods of production of stress proteins using tin or zinc metal ions. The invention relates to methods of protecting a mammal against injury caused by a noxious condition by administering to the mammal tin or zinc metal ions in sufficient quantity and under appropriate conditions to induce production of stress proteins at sufficient levels to provide partial or complete protection against injury caused by a noxious condition which occurs subsequent to stress protein production. The invention also relates to methods of inducing stress protein production in a mammal by administering tin or zinc metal ions in sufficient quantity and under appropriate conditions to induce production of stress proteins to protect the mammal against injury caused by a noxious condition. The invention also relates to compositions comprising tin or zinc metals, stress proteins, and/or agents which enhance or prolong the activity of stress proteins or which aid in the uptake of the heavy metal ions into the tissue.

20 Claims, No Drawings

OTHER PUBLICATIONS

Neil, Teresa K. et al., "Differential Heme Oxygenase Induction by Stannous and Stannic Ions in the Heart," *J. of Cell. Biol.*, vol. 57:409–414 (1995).

Levinson, Warren et al., "Metal Binding Drugs Induce Synthesis of Four Proteins in Normal Cells," *Bio. Trace Element Res.*, vol. 1:15–23 (1979).

Welch, William J. et al., "Biochemical Characterization of the Mammalian Stress Proteins and Identification of Two Stress Proteins as Glucose– and $Ca^{2+}$ – Ionophore–regulated Proteins," *J. Bio. Chem.*, vol. 258, No. 11:7102–7111 (1983).

Young, Richard A. and Elliott, Timothy J., "Stress Proteins, Infection, and Immune Surveillance," *Cell*, vol. 59:5–8 (1989).

Koenig, William J. et al., "Improving Acute Skin–Flap Survival Through Stress Conditioning Using Heat Shock and Recovery," *Plastic and Reconstructive Surgery*, vol. 90, No. 4:659–664 (1992).

Hotchkiss, Richard et al., "Hyperthermia protects mice against the lethal effects of endotoxin," *Am. J. Physiol.*, 265 (*Regulatory Integrative Comp. Physiol. 34*):R1447–R1457 (1993).

Conners, Michael S. et al., "A Closed Eye Contact Lens Model of Corneal Inflammation," *Investigative Ophthalmology & Visual Science*, vol. 36(5):841–850 (1995).

Perdrizet, George A. et al., "Surgical Stress and the Heat Shock Response," *Abstract, Cold Spring Harbor Laboratory Symposium on Molecular Chaperones and the Heat Shock Response*, Cold Spring Harbor, New York, May 1–5, 1996, p. 240.

Perdrizet, George A. et al., "The Heat Shock Response Protects Organs from Preservation Injury," *Poster, IMEDEX 4th Basic Sciences Symposium of the Transplantation Society*, Noordwijkerhout, The Netherlands, Sep. 17–20, 1995.

Neil, Teresa, K. et al., "Modulation of Corneal Heme Oxygenase Expression by Oxidative Stress Agents," *Journal of Ocular Pharmacy and Therapeutics*, vol. 11, No. 3: 455–468 (1995).

Abraham, N.G. et al., "Transfection of the Human Heme Oxygenase Gene into Rabbit Coronary Microvessel Endothelial Cells: Protective Effect Against Heme and Hemoglobin Toxicity," *Proc. Natl. Acad. Sci. USA*, vol. 92, 6798–6802 (1995).

Mitani, Kinuko et al., "The Role of Inorganic Metals and Metalloporphyrins in the Induction of Haem Oxygenase and Heat–shock Protein 70 in the Human Hepatoma Cells," *Biochem. J.* (England) vol. 290:819–825 (1993).

Levere, R.D., et al., "Amelioration of Hemorrhage Induced Brain Injury by Tin–Protoporphyrin," *J. Cell. Biol. 107* (6 Part 3): 726a (1988) Abstract 4116.

DaSilva, Jean–Louis et al., "Dual Role of Heme Oxygenase in Epithelial Cell Injury: Contrasting Effects of Short–term and Long–term Exposure to Oxidant Stress," *J Lab Clin Med* vol. 128, No. 3:290–296 (1996).

Levere, Richard, D. et al., "Role of Heme Oxygenase in Heme–Mediated Inhibition of Rat Brain $Na^+$–$K^+$–ATPase: Protection by Tin–Protoporphyrin," *Neurochemical Research*, vol. 14, No. 9:861–864 (1989).

DaSilva, Jean–Louis, et al., "Tin–Mediated Heme Oxygenase Gene Activation and Cytochrome P450 Arachidonate Hydroxylase Inhibition in Spontaneously Hypertensive Rats," *The American Journal of the Medical Sciences*, vol. 307, No. 3: 173–181 (1994).

Lutton, John D. et al., "Coexpression of Erythropoietin and Heme Oxygenase Genes in Hep3B Cells," *Hepatology*, vol. 17, No. 5:861–868 (1993).

Levere, R.D. et al., "Role of Heme Oxygenase in Hemoglobin–Mediated Inhibition of Brain $Na^+$–$K^+$–ATPase: Protection by Tin–Protoporphyrin", *Clin. Res.* vol. 36, No. 3:549a (1988) Abstract.

Stoltz, R. et al., "Heme Oxygenase May be an Important Protector Against Oxidative Stress–Associated Rise in ICAM Expression in Endothelial Cells," *Clin. Res. Mtg., J. of Invest. Med.*, vol. 43, No. 2(Suppl. 2):375A (1995).

Abraham, N.G. et al., "Transfection of the Human Heme Oxgenase Gene into Coronary Endothelial Cells Protects Against Heme/Hemoglobin Toxicity," *Clin. Res. Mtg., J. of Invest Med.*, vol. 43, No. 2(Suppl. 2):215A (1995).

Neil, T.K. et al., "Corneal Epithelial Heme Oxygenase: A Potential Protective Enzyme Against Oxidative Stress–Induced Injury," *Invest. Opthal. & Vis. Sci.*, vol. 36, No. 4 (1995) Abstract 2424–391.

Sessa, William, C. et al., "Manipulation of Cytochrome P–450 Dependent Renal Thromboxane Synthase Activity in Spontaneously Hypertensive Rats," *Journal of Hypertension*, vol. 7, No. 1: 37–42 (1989).

Sacerdoti, D. et al., "Treatment with Tin Prevents the Development of Hypertension in Spontaneously Hypertensive Rats," *Science*, vol. 243:388–390 (1989).

Kappas et al, "Tin: A potent inducer of heme oxygenase in kidney", *Science*, vol. 192:60–62. (1976).

Stocker R., "Induction of Haemoxygenase as a defense against oxidative stress," *Free Rad. Res. Comms*, vol. 9:101–112 (1990).

Vile G.F. et al, "Hemeoxygenase 1 mediates an adaptive response to oxidative stress in human skin fibroblasts,", *Proc. Natl. Acad. Sci.* (*USA*), vol. 91:2607–2610 (1994).

Hart, B.A., "Cross–tolerance to hyperoxia following cadmium aerosol pretreatment," *Toxicol Applied Pharmaco*, vol. 103:255–70 (1990).

Matsubara J. et al, "Protective effect of zinc against lethality in irridiated mice," *Environ. Res.*, vol. 41:558–67 (1986).

Goering, P.L., "Stress protein synthesis induced by cadmium–cysteine in rat kidney," *Toxicology*, vol. 85:25–39 (1993).

Levinson, W., "Transition series metals and sulfhydryl reagents induce the synthesis of four proteins in eukaryotic cells," *Biochemica et Biophys, Acta*, vol. 606:170–180 (1980).

Willis "Expression and modulatory effects of heme oxygenase in acute inflammation in the rat", Inflamm. Res. (1995) 44(Suppl 2): S218–220.

Thomas, Ed. Taber's Cyclopedic Medical Dictionary (1985) (F.A. Davis Co.Philadephia), p. 814.

Yamada et al. "Induction of 70–kDa protein in human lymphocytes exposed to inorganic heavy metals and toxic organic compounds", Toxicology (1993) 79:131–138.

Goering et al. "Metals and Stress Proteins" in Toxiclogy of Metals: Biochemical Aspects (1995) (Springer–Verlag: Berlin) 115: 229–266.

Powell et al. "Zinc improves postischemic recovery of isolated rat hearts through inhibition of oxidative stress," Am. J. Physiol. (1994) 266(35): H2497–H2507.

Yoshikawa et al. "Effect of zinc–carnosine chelate compounds (Z–103), a novel antioxidant, on acute gastric mucosal injury induced by ischemia–reperfusion in rats," Free Radical Res. Comm. (1991) 14(4): 289–96 (abstract only).

METHODS AND COMPOSITIONS FOR INDUCING PRODUCTION OF STRESS PROTEINS

DESCRIPTION

BACKGROUND OF THE INVENTION

Individuals are affected by a wide variety of insults and traumas, such as reperfusion and ischemia. It would be helpful to have additional methods or techniques for aiding individuals in their response to such events.

SUMMARY OF THE INVENTION

The present invention relates to compositions and methods of production of stress proteins using heavy metal ions. The invention relates to methods of protecting a mammal against injury caused by a noxious condition by administering to the mammal a heavy metal in sufficient quantity and under appropriate conditions to induce production of stress proteins at sufficient levels (in sufficient quantity) to provide protection (partial or complete) against injury caused by a noxious condition which occurs subsequent to stress protein production. The invention also relates to methods of inducing stress protein production in a mammal by administering a heavy metal in sufficient quantity and under appropriate conditions to induce production of stress proteins to protect the mammal against injury caused by a noxious condition.

Noxious conditions are those which cause injury or damage to organs, tissues or cells in animals, including human and nonhuman animals, plants, foods, and any other substance that comprises living matter or that is derived from living matter. Such noxious conditions include, but are not limited to, ischemia, reperfusion, hyperthermia, hypothermia, toxemia, oxygen and nutrient deprivation, heavy metal toxicity, ethanol toxicity, and superoxide radicals. The heavy metal is administered sufficiently prior to the injury to allow time for the production of stress. Heavy metals which are relatively nontoxic to humans, such as tin and zinc, are administered in particular embodiments. In one particular embodiment, stannous chloride is administered. Particular routes of administration include subcutaneous injection and intraperitoneal injection.

The invention also relates to compositions comprising heavy metals, stress proteins, and/or agents which enhance or prolong the activity of stress proteins or which aid in the uptake of heavy metal into the tissue.

DETAILED DESCRIPTION OF THE INVENTION

Change in gene expression induced by cellular stress is known as heat shock reponse (HSR). It is a phenomenon in which adaptive, reversible changes in cellular metabolism are rapidly induced after exposure to a cellular stress. The development of the response is associated with a temporary period of protection, during which the cell, tissue, or organ is protected from what would otherwise be irreversible injury. The purposeful induction of the cellular stress response to protect living tissues from the injurious effects of stress is known as stress conditioning.

Several features are of interest in the context of the present invention. First, HSR is a universally prevalent, fundamental response occurring in all species studied from bacteria to humans. Therefore, it is likely that any cell type can be protected against injury given the correct manipulation of this response. Second, following the induction of stress protein production, the cell, tissue, and whole organism are protected against the injurious effects of a subsequent lethal exposure to the stressful agent (i.e., a state of acquired tolerance to stress has been induced). Third, cross protection (also known as cross-resistance or cross-tolerance) exists. That is the conditioning stressful agent (e.g., a heavy metal) can confer protection against other forms of seemingly unrelated stress, such as cold ischemia, hypoxia, tumor necrosis factor, and various cellular toxins. This means that even if the exact nature of the harmful condition or noxious agent is not understood, it is still possible to provide protection against it. Fourth, a period of near-normal homeostasis is required to permit maximal development and expression of the protective response.

This invention relates to inducing stress protein production in a mammal by administering to the mammal a heavy metal in sufficient quantity and under appropriate conditions to induce stress protein production. The stress proteins are produced in sufficient quantity to produce the desired effect of protection against a subsequent noxious condition. The invention also relates to protecting a mammal against injury caused by a noxious condition by administering to the mammal a heavy metal in sufficient quantity and under appropriate conditions for production of stress proteins in sufficient quantity to protect against injury caused by the noxious condition.

As used herein, a "stress protein", also known as a "heat shock protein" (HSP) is a protein encoded by a stress gene; it is typically produced in significantly greater amounts upon contact or exposure to a source of stress. A "stress gene", or "heat shock gene", is used herein to mean a gene that is activated or otherwise detectably upgraded by contact or exposure to the source of stress.

One such stress protein is heme oxygenase (HO), or heat shock protein 32 kd. Heme oxygenase is an enzyme which participates in degradation of heme to biliverdin, which then can be broken down to bilirubin, a highly effective antioxidant. There are two heme oxygenase isoenzymes, which are the products of two distinct genes. Heme oxygenase-1 (HO-1) is the inducible form. Heme oxygenase-2 (HO-2) is a constitutively expressed form which is not induced by HO-1 inducers. HO-1 induction results in decrease in microsomal heme and consequent modulation of important cellular functions. A binding site for the oxidative stress response factor NF-kb is located in the human HO-1 promoter region. Induction of HO-1 during oxidative stress may restore the antioxidant/prooxidant ratio inside the cell.

"Protection" can be partial or complete, and, as a result, the effects of the injury are less than they would otherwise be if the stress protein production had not been induced.

A "heavy metal" is defined herein as a metal with an atomic number greater than 18, for example, mercury, cadmium, tin, lead, zinc, arsenic and copper.

The heavy metal may be administered in a compound. For example, a "tin containing compound" is intended to encompass a chemical composition containing tin in any oxidation state, including the stannous oxidation state and the stannic oxidation state. The compound can include a conjugate base of a mineral or organic acid. A "conjugate base of a mineral or organic acid" is intended to include, but not be limited to, chloride, sulfide, citrate, acetate and sulfate. Within the formulae represented herein, X is the conjugate base of a mineral or organic acid. $X_n$ is intended to encompass any combination of anions of any valency which is sufficient to balance the charge of the metal cation. For example, $X_2$ is intended to encompass either a single divalent anion or two monovalent anions. Compounds including X can further be defined to include additional solvent molecules or neutral Lewis bases. The anions can be chelating or multidentate, such as oxalate $(2^-)$.

Factors to be considered in determining how a heavy metal will be administered for production of stress proteins include the time before injury, the dosage of heavy metal and any accompanying agent, and route of administration. Appropriate conditions are those, including timing of administration of the heavy metal, which result in production of a sufficient quantity of the heavy metal to provide the desired effect (protection against the injury from the noxious condition).

For a heavy metal to be administered sufficiently prior to injury, it must be administered sufficiently prior to injury to allow for the production of sufficient stress proteins to protect against injury, but should not be administered so far in advance of the injury that the stress protein level is not sufficient to provide the protection desired. This time frame is generally from one hour to one week, depending on the organism, the noxious condition, the heavy metal, and the conditions of administration.

The dosage of heavy metal or any accompanying agent administered will, of course, vary depending upon known factors such as the pharmacodynamic characteristics of the heavy metal or particular agent, and its mode and route of administration; age, health, and weight of the recipient; nature and extent of symptoms, kind of concurrent treatment, frequency of treatment, and the effect desired. One dosage is approximately 0.15 mg/kg. of the recipient.

The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of heavy metals at the site of treatment include, but are not limited to, parenteral routes such as intradermal, intramuscular, intraperitoneal, intravenous, subcutaneous, intramedullary, and intranasal; and nonparenteral routes such as oral and rectal. Other suitable methods include biodegradable devices and slow release polymeric devices.

For parenteral administration, heavy metals can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques. Suitable pharmaceutical carriers are described in the most recent edition of Remington's Pharmaceutical Sciences, A. Osol, a standard reference text in this field of art.

The heavy metal can be administered alone or in compositions which comprise, in addition to the heavy metal, stress proteins and/or one or more agents which enhance or prolong the activity of stress proteins or one or more agents which aid in the uptake of the heavy metal into the desired tissue. These compositions are also the subject of the present application. Such agents may include, but are not limited to, chelating agents, antioxidants, and allopurinol. An antioxidant as defined herein is an agent that inhibits oxidation.

A "noxious condition" is defined herein as any condition which causes an injury or damage to organs, tissues or cells in animals, including human and nonhuman animals, plants, foods, and any other substance that comprises living matter or that is derived from living matter. Such noxious conditions include, but are not limited to, ischemia, reperfusion, hyperthermia, hypothermia, toxemia, oxygen and nutrient deprivation, heavy metal toxicity, ethanol toxicity, and superoxide radicals.

Ischemia is anoxia or local anemia due to obstruction of blood flow. The loss of blood flow through tissues results in the buildup of toxic metabolic waste products and is associated with the loss of intracellular high energy compounds and acidosis. Ischemia causes a marked decrease in the intracellular content of high energy phosphates. The loss of cellular energy stores results in mitochondrial dysfunction and a reduction of $Na^+/K^+$-ATPase pump activity which in turn leads to a disruption of the normal electrochemical gradients across cellular membranes. The net result is an influx of $Na^+$ ions and water into the cell. Loss of ionic gradients disrupts membrane transport functions and signaling. Cellular membranes become abnormally permeable and a rapid influx of $Ca^{2+}$ ions occurs, resulting in uncontrolled enzymatic activation and irreversible protein denaturation. Cell death occurs by both necrotic and apoptotic pathways. Ischemia can increase oxidant injury as well, by decreasing the levels of native free radical scavengers, such as superoxide dismutase, glutathione and catalase, and by increasing production of toxic reactive oxygen intermediates, also known as reactive oxygen species or superoxide radicals.

Reperfusion is the re-passage of blood or other fluid through a vascular bed. Reperfusion injury is fundamentally an inflammatory lesion and, therefore, may represent a nonspecific inflammatory response which occurs as ischemic tissues become reoxygenated. This is due largely to the endogenous production of toxic reactive oxygen intermediates, which provide direct and indirect damage to cellular membranes, enzymes, and nuclear contents. They can cause lipid peroxidation and initiate a chain reaction of auto-oxidation events leading to membrane damage. This permits excessive calcium influx into the cell, uncontrolled enzymatic activation, and eventual cell death.

The common thread linking a number of these injury syndromes, such as noncardiogenic pulmonary edema following cardiopulmonary bypass, hemorrhagic shock and trauma, organ preservation and acute allograft rejection, may be oxidant injury. The human body has intrinsic antioxidant protection, including the mitochondrial-cytochrome oxidase system, enzymatic forms including superoxide dismutase (SOD), catalase, glutathione peroxidase, and heme oxygenase, and nonenzyme forms.

The purpose of HSR may be to protect the host tissues against inflammatory responses designed to destroy invading organisms. HSR causes preservation of glutathione reductase levels and induction of superoxide dismutase activity, both of which could conceivably provide protection to the ischemic organ subjected to reperfusion. Stress proteins avidly bind adenosine triphosphate (ATP) and to be involved in transportation of proteins across mitochondrial and other cellular and subcellular membranes. Also, stress proteins function in unstressed cells as molecular chaperones which guide and assist in the proper folding and translocation of complex protein molecules within and between cellular compartments. The HSR may involve the peptide binding functions of stress proteins which may prevent intracellular protein denaturization and allow transmembrane transportation of macromolecules during times of stress.

Ischemia and reperfusion are caused by a number of events, including many modern invasive surgical and medical techniques which result in the interruption of blood flow to tissues and organs. For example, the methods of the present invention would be useful for treatment of surgical procedures such as cardiopulmonary bypass, coronary artery bypass, peripheral vascular bypass, and coronary artery angioplasty. In each of these situations, organs and tissues are consistently damaged through ischemia and reperfusion.

In addition, many therapeutic agents used in clinical medicine expose organs and tissues to toxic side effects. Cellular protection by the present invention can prevent organ and tissue damage from drug related toxicities. One such example is the use of intravenous radiocontrast materials currently used in x-ray imaging. These compounds are known to be toxic to the kidney and frequently induce renal dysfunction in patients. It is possible to protect kidneys from injury due to radiocontrast material if the stress response is induced prior to patients receiving these toxic agents. In a similar fashion, undesirable toxic side effects of current chemo- and radiation therapies for cancer could be prevented or reduced by the present invention. The invention can also be used to protect against necrosis of pedicled skin flaps in plastic surgery, caused by inadequate blood flow within the flap.

Induction of stress proteins by the present invention will protect tissues and organs from acute global inflammatory states. For example, it can protect isolated cells from cytotoxicity by mediators of sepsis such as interleukin-1, tumor necrosis factor, and bacterial endotoxins. Sepsis is the systemic inflammatory response to infection. There are a number of patients who are readily identifiable as being at high risk for developing sepsis, such as those with multiple trauma, patients on mechanical ventilators, premature babies, and immunosuppressed patients.

Induction of heat shock proteins by heavy metals including stannous chloride can serve a number of other purposes as well, such as the enhanced preservation of fruits, fish and meats for storage and transportation since many of these foods spoil due to oxidant injury. It may also be possible to stress condition individuals using the present invention prior to conditions of extreme physical activity such as those that are encountered during surgery, battle or war, sporting events or space flight. Successful stress conditioning would allow individuals to temporarily survive lethal forces or injuries.

In addition, the teachings of the present invention can be used to assay for the ability of an animal to produce certain stress proteins, and for research about stress proteins.

The present invention will now be illustrated by the following examples, which are not intended to be limiting in any way.

EXAMPLE I

Acute Spinal Cord Ischemia in the Rabbit
Materials and Methods
New Zealand White rabbits were stress conditioned and subjected to spinal cord ischemia using methods similar to those previously described in Chatson et al., "Heat shock protects kidneys against warm ischemic injury", *Current Surgery*, 47(6): 420–423 (November–December 1990), the contents of which are incorporated herein by reference in their entirety. The rabbits were subjected to spinal cord ischemia by occlusion of the infrarenal-abdominal aorta as an ischemic insult to the spinal cord, for 20 minutes at 37° C. The occlusion was then removed and blood flow re-established to the infra-renal aorta. Neurological function of the lower extremities was then evaluated 24 hours after reperfusion. Control animals were consistently paralyzed. Animals stress conditioned with whole body hyperthermia showed intact neurologic function in eight of eight animals tested. Four animals were pretreated with an intraperitoneal injection in the rump region of stannous chloride ($SnCl_2$) in a saline diluent at a dose of 0.15 mg per kilogram, sixteen hours prior to aortic occlusion. Twenty four hours after reperfusion, all four of these animals had intact neurologic function.

EXAMPLE II

Warm Ischemic Injury of the Rat Kidney
Materials and Methods
Male Sprague-Dawley rats were stress conditioned and subjected to warm ischemic injury using methods similar to those previously described in Chatson et al., infra. The non-treated control animals underwent 60 minutes of occlusion of the renal artery as an ischemic insult. Following the ischemic injury, flow was re-established in the kidney and vascular resistance of the kidney was meausred. To measure renal vascular resistance, a syringe system was set up through the renal artery, to give a constant flow rate of approximately 0.5 cc/minute. Since there was a constant flow rate, it was possible to measure the pressure generated in the syringe. The higher the pressure, the greater the resistance. Flow rate was recorded as mm mercury/ml fluid/gram of tissue.
Results
Renal vascular resistance of the uninjured nonischemic kidney averages approximately 43–44 resistance units. Following 60 minutes of warm renal ischemia, this resistance increased to approximately 60 resistance units in the control group. The kidneys that were previously stress conditioned through whole body hyperthermia prior to warm renal ischemia, demonstrated a remarkable preservation of renal vascular resistance of 37 resistance units. The kidneys that were stress conditioned with stannous chloride demonstrated a renal vascular resistance of 45 resistance units following 60 minutes of warm ischemic injury.
Equivalents
Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A method for protecting a mammal from injury due to hyperthermia, hypothermia, ischemia or reperfusion comprising administering to the mammal an effective amount of a composition comprising tin ions.

2. The method of claim 1 wherein the composition is administered sufficiently prior to the injury for the production of stress proteins in sufficient quantity to protect the mammal against the injury.

3. The method of claim 1 wherein the composition comprises tin in the stannous oxidation state.

4. The method of claim 1 wherein the composition comprises tin in the stannic oxidation state.

5. The method of claim 1 wherein the composition comprises $SnX_2$, wherein X is a conjugate base of a mineral or organic acid.

6. The method of claim 1 wherein the composition comprises $SnX_4$, wherein X is a conjugate base of a mineral or organic acid.

7. The method of claim 1 wherein administering the composition to the mammal is accomplished via a route selected from the group consisting of intradermal, intramuscular, intraperitoneal, intravenous, subcutaneous, intramedullary and intranasal.

8. A method for protecting a mammal from injury due to hyperthermia or hypothermia comprising administering to the mammal an effective amount of a composition comprising zinc ions.

9. The method of claim 8 wherein the composition is administered sufficiently prior to the injury for the production of stress proteins in sufficient quantity to protect the mammal against the injury.

10. The method of claim 8 wherein the composition comprises $ZnX_2$, wherein X is a conjugate base of a mineral or organic acid.

11. The method of claim 8 wherein administering the composition to the mammal is accomplished via a route selected from the group consisting of intradermal, intramuscular, intraperitoneal, intravenous, subcutaneous, intramedullary and intranasal.

12. A composition comprising tin ions and at least one agent selected from the group consisting of a) agents which enhance the activity of stress proteins; b) agents which prolong the activity of stress proteins; and c) agents which aid in the uptake of the tin ions into oxidant-damaged tissue, provided that the agent is not an antioxidant or a chelating agent.

13. The composition of claim 12 wherein the tin ions are in the stannous oxidation state.

14. The composition of claim 12 wherein the tin ions are in the stannic oxidation state.

15. The composition of claim 12 wherein the composition comprises $SnX_2$, wherein X is a conjugate base of a mineral or organic acid.

16. The composition of claim 12 wherein the composition comprises $SnX_4$, wherein X is a conjugate base of a mineral or organic acid.

17. A method of inducing stress protein production in a mammal comprising administering to the mammal a tin ion in sufficient quantity and under appropriate conditions to induce production of stress proteins for the purpose of protecting against injury from a noxious condition in the mammal, wherein the noxious condition is selected from the group consisting of ischemia, reperfusion, hyperthermia and hypothermia.

18. A method of inducing stress protein production in a mammal comprising administering to the mammal a zinc ion in sufficient quantity and under appropriate conditions to induce production of stress proteins for the purpose of protecting against injury from a noxious condition in the mammal, wherein the noxious condition is selected from the group consisting of hypothermia and hyperthermia.

19. A method of protecting a mammal from injury caused by ischemia and reperfusion comprising administering to the mammal an effective amount of a composition comprising tin ions.

20. A method of inducing stress protein production in a mammal comprising administering to the mammal a tin ion in sufficient quantity and under appropriate conditions to induce production of stress proteins for the purpose of protecting against injury caused by ischemia and reperfusion.

* * * * *